United States Patent [19]

Karrer et al.

[11] Patent Number: 5,792,825

[45] Date of Patent: Aug. 11, 1998

[54] SILICONE COMPOUNDS CONTAINING STERICALLY HINDERED CYCLIC AMINE FUNCTIONAL GROUPS WHICH ARE USEFUL FOR THE LIGHT AND THERMAL STABILIZATION OF POLYMERS

[75] Inventors: Philippe Karrer; Gérard Mignani, both of Lyons; Bernard Pontini, St-Symphorien D 'Ozon; Storet Isabelle, Les Eparres, all of France

[73] Assignee: Rhone-Poulenc Chimie, Courbevoie, France

[21] Appl. No.: 661,692

[22] Filed: Jun. 11, 1996

[30] Foreign Application Priority Data

Jun. 16, 1995 [FR] France ................... 95 07445

[51] Int. Cl.$^6$ ................... C08G 77/04
[52] U.S. Cl. ................... 528/27; 528/28; 528/33; 528/125; 528/220; 528/100; 528/103; 528/88; 528/92 G
[58] Field of Search ................... 528/27, 28, 33, 528/125, 220; 525/100, 103, 88, 92 G

[56] References Cited

FOREIGN PATENT DOCUMENTS

| | | | |
|---|---|---|---|
| 0 343 717 | 11/1989 | European Pat. Off. | ......... C08G 77/38 |
| 0 358 200 | 3/1990 | European Pat. Off. | ......... C08L 23/02 |
| 0 491 659 | 6/1992 | European Pat. Off. | ......... C08G 77/26 |
| 0 581 520 | 2/1994 | European Pat. Off. | ......... C08L 71/12 |
| 96 16110 | 5/1996 | France . | |
| 96 16124 | 5/1996 | France . | |
| 96 16127 | 5/1996 | France . | |
| 96 18667 | 6/1996 | France . | |

*Primary Examiner*—Duc Truong
*Attorney, Agent, or Firm*—Andrew M. Solomon

[57] ABSTRACT

The present invention relates to linear, cyclic or branched polyorganosiloxanes having, per molecule, at least three siloxy units, including at least one functional unit of formula:

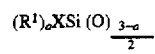

where $R^1$ represents a $C_1$ to $C_4$ alkyl or phenyl radical and X contains a secondary or tertiary cyclic amine functional group bonded to the silicon via an Si—A—C bond where A is a residue comprising a cyclic acetal group. X more specifically represents a monovalent group of formula:

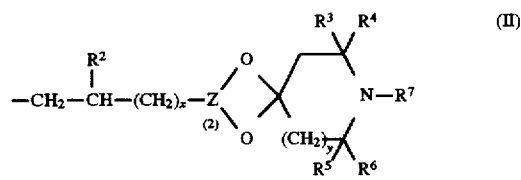

The present invention also relates to the use of such polyorganosiloxanes in polymers for improving in particular their photostabilization.

18 Claims, No Drawings

SILICONE COMPOUNDS CONTAINING STERICALLY HINDERED CYCLIC AMINE FUNCTIONAL GROUPS WHICH ARE USEFUL FOR THE LIGHT AND THERMAL STABILIZATION OF POLYMERS

The present invention relates, in its first subject, to new silicone compounds comprising, per molecule, at least one sterically hindered cyclic amine functional group bonded to the silicon atom via an Si—A—C bond where A is a residue comprising a cyclic acetal group; it also relates, in its first subject, to silicone compounds comprising, per molecule, at least one sterically hindered cyclic amine functional group bonded to the silicon atom via an Si—A—C bond and at least one other compatibilizing functional group bonded to the silicon via an Si—C bond. It also relates, in a second subject, to a process for the preparation of the said silicone compounds. It further relates, in a third subject, to the use of such compounds in polymers for improving their resistance to degradation under the effect of ultraviolet (UV) radiation, of atmospheric oxygen and of heat.

Indeed, organic polymers, and more particularly polyolefins and polyalkadienes, degrade when they are subjected to external agents and in particular to the combined effect of air and of solar ultraviolet radiation.

This degradation is generally limited by the introduction into the polymer of small amounts of stabilizing agents.

Among these UV stabilizers, sterically hindered cyclic amines, in particular 2,2,6,6-tetramethylpiperidines, are currently among the most effective.

However, in practice, one of the major problems relating to the use of these UV stabilizers is to obtain a good compromise between their effectiveness, which involves their mobility within the polymer, and the permanence of their effect, which involves the use of molecules with a high molecular mass having excellent compatibility with the polymers to be stabilized.

It has been proposed in the prior state of the art to resort advantageously to polyorganosiloxanes carrying sterically hindered piperidyl functional groups. Mention may be made, as documents illustrating this prior art, of, for example, the documents Patents JP-A-01/096259, EP-A-0,338,393, EP-A-0,343,717, EP-A-0,358,190, EP-A-0,388,321 and EP-A-0,491,659.

However, to the knowledge of the Applicant Company, no document of the prior art describes polyorganosiloxanes which, on the one hand, have a structure in which each sterically hindered cyclic amine functional group is bonded to the silicon atom via an Si—A—C bond where A is a residue comprising a cyclic acetal group and, on the other hand, are endowed with properties which are useful for improving the resistance of the polymers to degradation under the effect of UV radiation, of atmospheric oxygen and of heat.

More precisely, the present invention relates, in its first subject, to a polyorganosiloxane comprising, per molecule, at least 3 siloxy units, including at least one siloxy functional unit of formula:

  (I)

in which:
the symbols $R^1$ are identical or different and represent a monovalent hydrocarbon radical chosen from the linear or branched alkyl radicals having from 1 to 4 carbon atoms and the phenyl radical;

the symbol X represents a monovalent group of formula:

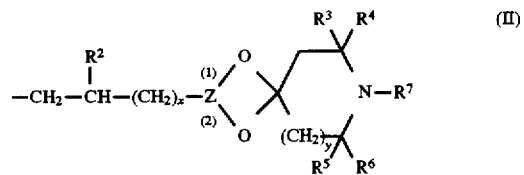  (II)

in which:
$R^2$ represents a hydrogen atom or a linear or branched alkyl radical having from 1 to 3 carbon atoms;

the symbol Z represents a trivalent group comprising at least 3 carbon atoms and which is: a substituted or unsubstituted, saturated or ethylenically unsaturated aliphatic radical which can contain at least one carbonyl group bonded via its free valencies to two atoms constituting the cyclic acetal group:

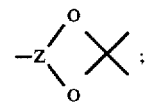

or a substituted or unsubstituted monocyclic aromatic radical; or a substituted or unsubstituted condensed polycyclic aromatic radical; or a polycyclic aromatic radical containing a number of substituted or unsubstituted, condensed or non-condensed cyclic systems which are bonded to one another via valency bonds or via atoms or groups; the atoms or groups which can connect these aromatic cyclic systems can be, for example, oxygen and sulphur atoms or groups composed of linear or branched alkylene radicals having from 1 to 3 carbon atoms and the —CO—, —SO$_2$—, —CONH—, —NH— or —COO— groups;

the (1) and (2) bonds leaving from the symbol Z relate to adjacent carbon atoms when Z represents an aromatic radical and to adjacent carbon atoms or carbon atoms which are in the A position with respect to one another when Z represents an aliphatic radical;

the $R^3$, $R^4$, $R^5$ and $R^6$ radicals, which are identical or different, are chosen from the linear or branched alkyl radicals having from 1 to 3 carbon atoms, the phenyl radical and the benzyl radical;

$R^7$ is chosen from a hydrogen atom, the linear or branched alkyl radicals having from 1 to 12 carbon atoms, the alkylcarbonyl radicals where the alkyl residue is a linear or branched residue having from 1 to 8 carbon atoms, the phenyl and benzyl radicals and an O. radical;

x is an integer chosen from 0, 1, 2 and 3;
y is an integer chosen from 0 and 1;
a is a number chosen from 0, 1 and 2.

The polyorganosiloxane can additionally have at least one other functional unit of formula:

  (III)

in which
the symbols $R^1$ have the same meanings as those given above with respect to the formula (I);

the symbol W represents a monovalent group containing a compatibilizing functional group chosen from: a linear or branched alkyl radical having more than 4 carbon atoms; a radical of formula —$R^8$—COO—$R^9$ in which $R^8$ represents a linear or branched alkylene radical having from 5 to 20 carbon atoms and $R^9$ represents a linear or branched alkyl radical having from 1 to 12 carbon atoms; a radical of formula —$R^{10}$—O—($R^{11}$—O)$_c$—$R^{12}$ in which $R^{10}$ represents a linear or branched alkylene radical having from 3 to 15 carbon atoms, $R^{11}$ represents a linear or branched alkylene radical having from 1 to 3 carbon atoms, c is a number from 0 to 10 and $R^{12}$ represents a hydrogen atom, a linear or branched alkyl radical having from 1 to 12 carbon atoms or an acyl radical —CO—$R^{13}$ where $R^{13}$ represents a linear or branched alkyl radical having from 1 to 11 carbon atoms;

b is a number chosen from 0, 1 and 2.

The other possible siloxy unit(s) of the polyorganosiloxane correspond(s) to the formula:

$$(R^1)_d(H)_e Si(O)_{\frac{4-(d+e)}{2}} \quad (IV)$$

in which the symbols $R^1$ have the same meanings as those given above with respect to the formula (I);

d is a number chosen from 0, 1, 2 and 3;

e is a number chosen from 0 and 1;

the sum d+e is not greater than 3.

The siloxy units of formula (I), when there are more than two of them, can be identical to or different from one another; the same comment also applies to the siloxy units of formulae (III) and (IV).

In the present statement, the following definitions will be understood to apply:

"cyclic amine functional groups": monovalent X groups;

"compatibilizing functional groups": optional monovalent W groups which are directly bonded to the silicon atoms (in this case, Si—C bonds are then formed);

"mixed organopolysiloxanes (or polymers)": polymers which are equipped with both cyclic amine functional group(s) and compatibilizing functional group(s).

Taking into account the values which the symbols a, b, d and e can take, it should further be understood that the polyorganosiloxanes according to the invention can thus have a linear, cyclic or branched (resin) structure or a mixture of these structures. When it concerns linear polymers, the latter can optionally have up to 50 mol % of branching [units of "T" ($RSiO_{3/2}$) and/or "Q" ($SiO_{4/2}$) types].

When it concerns polyorganosiloxane resins, the latter are composed of at least two types of different siloxy units, namely "M" ($R_3SiO_{1/2}$) and/or "T" units and optionally "D" ($R_2SiO_{2/2}$) units; the number of "M" units/number of "Q" and/or "T" units ratio is generally between 4/1 and 0.5/1 and the number of "D" units/number of "Q" and/or "T" units ratio is generally between 0 and 100/1.

The numbers of the units of formulae (I), and optionally (III) and (IV), are advantageously such that the polyorganosiloxanes according to the invention contain:

at least 0.5 mol %, preferably from 8 to 90 mol %, of cyclic amine functional groups, and optionally at least 0.5 mol %, preferably from 8 to 90 mol %, of compatibilizing functional groups. The mol % values indicated express the number of moles of functional groups per 100 silicon atoms.

The preferred $R^1$ radicals are: methyl, ethyl, n-propyl, isopropyl or n-butyl; more preferentially, at least 80 mol % of the $R^1$ radicals are methyls.

The cyclic amine functional groups represented by the X groups are preferentially chosen from the radicals of formula (II) defined above in which the symbols $R^2$, $R^3$, $R^4$, $R^5$, $R^6$, $R^7$, x and y have the meanings given above with respect to the formula (II) and the symbol Z represents a trivalent radical chosen from:

an aliphatic radical of formula:

$$-CR^{14} \diagup_{CO-}^{CO-} \quad (II-1)$$

where the thick right-hand free valencies are connected to the oxygen atoms of the cyclic acetal group and $R^{14}$ represents a hydrogen atom, a linear or branched alkyl radical having from 1 to 3 carbon atoms or a radical of formula —$COOR^{14a}$ or —$NHCOR^{14a}$ where $R^{14a}$ represents a linear or branched alkyl radical having from 1 to 3 carbon atoms; and an aromatic radical corresponding to the following formulae:

(II-2); (II-3)

(II-4)

(II-5)

where the thick free valencies of each aromatic cyclic system are carried by two adjacent carbon atoms and $R^{15}$ represents —O—, —S—, a linear or branched alkylene group having from 1 to 3 carbon atoms, —CO—, —$SO_2$—, —CONH—, —NH— or —COO—.

More preferentially, the X groups containing a cyclic amine functional group are chosen from the X groups of formula (II) defined above in which:

$R^2$ represents a hydrogen atom or a methyl radical;

the symbol Z is a trivalent group of formula (II-1), where $R^{14}$ is a hydrogen atom, or of formula (II-2);

the $R^3$, $R^4$, $R^5$ and $R^6$ radicals, which are identical, are methyls;

the $R^7$ radical represents a hydrogen atom or a methyl radical;

x and y each represent an integer equal to 1.

The preferred optional compatibilizing functional groups W are chosen: from a linear or branched alkyl radical having from 5 to 18 carbon atoms; a radical of formula —$R^8$—COO—$R^9$ in which $R^8$ represents a linear or branched alkylene radical having from 8 to 12 carbon atoms and $R^9$ represents a linear or branched alkyl radical having from 1 to 6 carbon atoms; or a radical of formula —$R^{10}$—O—($R^{11}$—O)$_c$—$R^{12}$ in which $R^{10}$ represents a linear or branched alkylene radical having from 3 to 6 carbon atoms, $R^{11}$ represents a linear or branched alkylene radical having from 2 to 3 carbon atoms, c is a number from 0 to 6 and $R^{12}$ represents a hydrogen atom, a linear or branched alkyl radical having from 1 to 6 carbon atoms or an acyl radical —CO—$R^{13}$ where $R^{13}$ represents a linear or branched alkyl radical having from 1 to 5 carbon atoms.

The compatibilizing functional groups W are more preferentially chosen from the n-octyl, n-undecyl, n-dodecyl, n-tridecyl or methyl or ethyl decamethylenecarboxylate radicals.

The present invention, taken in its first subject, is more precisely still targeted at:

statistical, sequenced or block, linear, optionally mixed polydiorganosiloxane copolymers of average formula:

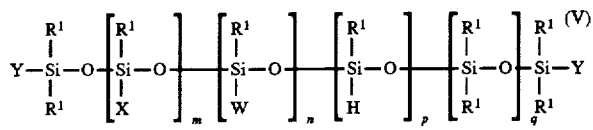

in which:
the symbols $R^1$, X and W have the general meanings given above with respect to the formulae (I) and (III);
the symbols Y represent a monovalent radical chosen from $R^1$, X, W and a hydrogen atom;
m is a whole or fractional number ranging from 0 to 180;
n is a whole or fractional number ranging from 0 to 180;
p is a whole or fractional number ranging from 0 to 10;
q is a whole or fractional number ranging from 0 to 100;
with the conditions according to which:
if m is other than 0 and, in the optional case of mixed polymers, if n is other than 0: the sum m+n+p+q lies in the range from 5 to 200; the ratio 100m/(m+n+p+q+2)≧0.5; and the ratio 100n/(m+n+p+q+2)≧0.5, this ratio being identical to or different from the preceding ratio;
if m=0 and, in the optional case of mixed polymers, if n is other than 0: at least one of the Y substituents represents the X radical; the sum m+n+p+q lies in the range from 5 to 100; and the ratio 100n/(m+n+p+q+2)≧0.5;
if m is other than 0 and n=0: the sum m+p+q lies in the range from 5 to 100; the ratio 100m/(m+p+q+2)≧0.5; and, in the optional case of mixed polymers, at least one of the Y substituents represents the W radical;
if m=0 and n=0: the sum p+q lies in the range from 5 to 100; one of the Y substituents being the X radical; and, in the optional case of mixed polymers, the other Y substituent being the W radical;

and those of average formula:

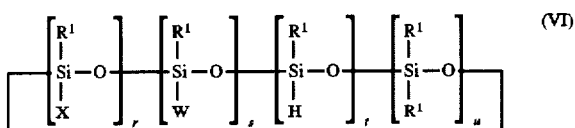

in which:
the symbols $R^1$, X and W have the general meanings given above with respect to the formulae (I) and (III);

r is a whole or fractional number ranging from 1 to 9;
s is a whole or fractional number ranging from 0 to 9;
t is a whole or fractional number ranging from 0 to 0.5;
u is a whole or fractional number ranging from 0 to 5;
the sum r+s+t+u lies in the range from 3 to 10.

The polymers of formula (V) which are preferred (so-called LP1 polymers) or highly preferred (so-called LP2 polymers) are those in which:
the symbols Y represent $R^1$;
m is a whole or fractional number ranging from 1 to 90;
n is a whole or fractional number ranging from 0 to 90;
p is a whole or fractional number ranging from 0 to 5;
g is a whole or fractional number ranging from 0 to 50;
the sum m+n+p+q is a whole or fractional number ranging from 10 to 100;
the ratio 100m/(m+n+p+q+2) lies in the range from 8 to 90;
with the condition according to which if n is other than 0, the ratio 100n/(m+n+p+q+2) lies in the range from 8 to 90, it being possible for this ratio to be identical to or different from the preceding ratio;
the $R^1$, X and W radicals simultaneously have the preferential definitions (in the case of LP1 polymers) or more preferential definitions (in the case of LP2 polymers) given above with respect to each of them.

The polymers of formula (VI) which are preferred (so-called CP1 polymers) or very preferred (so-called CP2 polymers) are those in which:
r is a whole or fractional number ranging from 1 to 4.5;
s is a whole or fractional number ranging from 0 to 4.5;
t is a whole or fractional number ranging from 0 to 0.25;
u is a whole or fractional number ranging from 0 to 2.5;
the sum r+s+t+u is a whole or fractional number ranging from 3 to 5;
the $R^1$, X and W radicals simultaneously have the preferential definitions (in the case of the CP1 polymers) or more preferential definitions (in the case of the CP2 polymers) given above with respect to each of them.

The polymers of formula (V), which are especially well-suited (so-called ELP1 polymers) or very especially well-suited (so-called ELP2 polymers) are the LP1 or LP2 polymers defined above in which the symbol n is a number ranging from 1 to 90.

The polymers of formula (VI), which are especially well-suited (so-called ECP1 polymers) or very especially well-suited (so-called ECP2 polymers) are the CP1 or CP2 polymers defined above in which the symbol s is a number ranging from 1 to 4.5.

The optionally mixed organopolysiloxanes of the invention can advantageously be obtained from, and this constitutes the second subject of the invention:
corresponding organohydropolysiloxanes (H), which are free of cyclic amine functional group(s) X and of compatibilizing functional group(s) W,
the organic compound(s) which is(are) ethylenically unsaturated at the chain end (ψ), from which the cyclic amine functional group(s) X derive(s),
and optionally the compound(s) which is(are) ethylenically unsaturated at the chain end (Ξ), from which the W functional group(s) derive(s).

Thus, the optionally mixed polyorganosiloxanes of the invention can be obtained by carrying out:
in the case of polymers containing solely cyclic amine functional group(s): an addition (hydrosilylation) reaction, or in the case of mixed polymers containing cyclic amine functional group(s) and containing compatibilizing functional group(s): two simultaneous or successive addition (hydrosilylation) reactions, starting with: the corresponding organohydropolysiloxanes (H) free of the X and W functional groups, the organic compound(s) which is(are) ethylenically unsaturated at the chain end ($\psi$), from which the X functional group(s) derive(s), and optionally the compound(s) which is(are) ethylenically unsaturated at the chain end ($\Xi$), from which the W functional group(s) derive(s).

These hydrosilylation reactions can be carried out at a temperature of the order of 20° to 200° C., preferably of the order of 60° to 120° C., in the presence of a catalyst based on a metal of the platinum group; mention may in particular be made of the platinum derivatives and complex described in U.S. Pat. No. 3,715,334, U.S. Pat. No. 3,814,730, U.S. Pat. No. 3,159,601 or U.S. Pat. No. 3,159,662.

The amounts of catalyst used are of the order of 1 to 300 parts per million, expressed as metal with respect to the reaction mixture.

In the definition of the "mol of ($\psi$)", the olefinic unsaturation capable of reacting with (H) by hydrosilylation will be regarded as the unit entity. Likewise, in the definition of the "mol of ($\Xi$)", the olefinic unsaturation capable of reacting with (H) by hydrosilylation will be regarded as the unit entity.

The amounts of reactants which can be used generally correspond to a [($\psi$)+optionally ($\Xi$)]/SiH [of (H)] molar ratio which is of the order of 1 to 5 and preferably of the order of 1 to 2.

The hydrosilylation reactions can take place in bulk or, preferably, in a volatile organic solvent such as toluene, xylene, methylcyclohexane, tetrahydrofuran, heptane, octane or isopropanol; the reaction mixture can additionally contain a buffer agent consisting in particular of an alkali metal salt of a monocarboxylic acid, such as, for example, sodium acetate.

At the end of the reactions, the crude optionally mixed polyorganosiloxanes which are obtained can be purified, in particular by passing through a column filled with an ion exchange resin and/or by simple evaporation of the reactants introduced in excess and optionally of the solvent used by heating between 100° and 180° C. under reduced pressure.

The organohydropolysiloxanes (H) which are used, for example, for the preparation of the linear mixed polydiorganosiloxanes of formula (V) are those of formula:

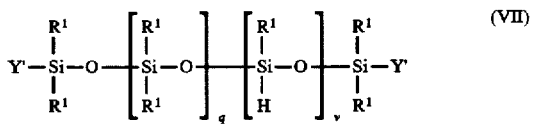
(VII)

in which:
the symbols $R^1$ and q have the general or preferential meanings given above with respect to the formula (V);
the symbols Y' represent $R^1$ or a hydrogen atom;
v is a whole or fractional number equal to m+n+p;
with the condition according to which, if v=0, q is a number lying in the range from 5 to 100 and then at least one of the Y' radicals represents a hydrogen atom.

The organohydropolysiloxanes (H) which are used, for example, for the preparation of the cyclic mixed polydiorganosiloxanes of formula (VI) are those of formula:

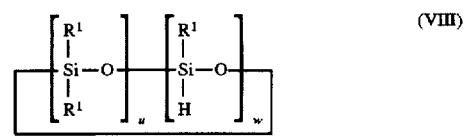
(VIII)

in which:
the symbols $R^1$ and u have the general or preferential meanings given above with respect to the formula (VI);
w is a whole or fractional number equal to r+s+t;
the sum u+w lies in the range from 3 to 10.

Such organohydropolysiloxanes (H) of formulae (VII) and (VIII) are known in the literature and some are commercially available.

The unsaturated organic compounds ($\psi$), from which the X groups containing a cyclic amine functional group derive, are the compounds of formula:

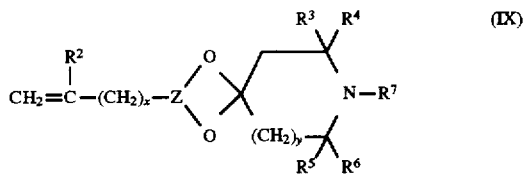
(IX)

in which the symbols $R^2$, Z, $R^3$, $R^4$, $R^5$, $R^6$, $R^7$, x and y have the general or preferential meanings given above with respect to the formula (II).

Mention may be made, as specific examples of compounds ($\psi$), of the compounds of formulae:

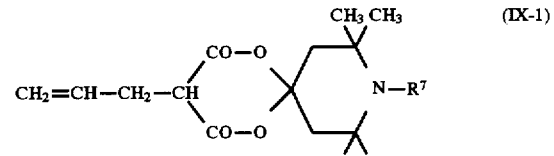
(IX-1)

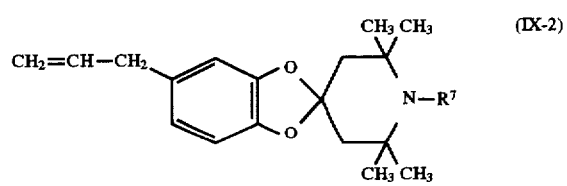
(IX-2)

in which $R^7$ is a hydrogen atom or a methyl radical.

The unsaturated organic compounds ($\psi$) of formula (IX), from which the X groups containing a cyclic amine functional group derive, are compounds which, to the knowledge of the Applicant Company, are novel products.

Unsaturated compounds ($\psi$) of formula (IX) in which the symbol Z represents an aliphatic residue can be prepared by reacting, in the presence of an acid catalyst:

an ortho-diphenol or an acetal of formula:

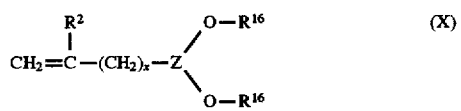
(X)

in which the symbols $R^2$, Z (aliphatic residue) and x have the general or preferential meanings given above with respect to the formula (II) and $R^{16}$ represents a hydrogen atom or a linear or branched alkyl radical having from 1 to 3 carbon atoms, with a ketone of formula:

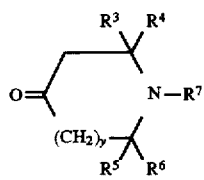

in which the symbols $R^3$, $R^4$, $R^5$, $R^6$, $R^7$ and y have the general or preferential meanings given above with respect to the formula (II).

As regards the way in which the abovementioned process is carried out in practice, reference should be made, for more details, to the contents of the following document which describes, starting from other reactants, a procedure applicable to carrying out the process under consideration: cf. Heterocycles, 32(3), page 529 et seq. (1991).

As regards the precursor ortho-diphenol or acetal of formula (X), it can be obtained by reacting:

a chlorinated compound of formula:

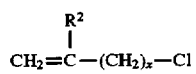

with an ortho-diphenol or an acetal of formula:

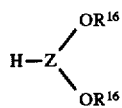

As regards the way in which this synthesis of the precursor ortho-diphenol or acetal of formula (X) is carried out in practice, reference should be made, for more details, to the contents of the following document: cf. Textbook of Practical Organic Chemistry, 5th edition (1989), page 682, Vogel, published by Longman.

As regards the precursor ketone of formula (XI), it corresponds to a known and commercially available product.

The scheme, which has just been described, for the synthesis of the different unsaturated compounds (ψ) of formula (IX) where Z represents an aliphatic residue applies particularly well when the symbol Z is the aliphatic radical of formula (II-1) mentioned above and x is an integer equal to 1, 2 or 3.

Unsaturated compounds (ψ) of formula (IX) in which the symbol Z represents an aromatic residue can be prepared by reacting, in the presence of an acid catalyst:

an ortho-diphenol of formula:

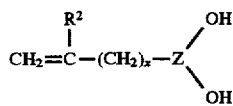

in which the symbols $R^2$, Z (aromatic residue) and x have the general or preferential meanings given above with respect to the formula (II), with
either an acetal of formula (transacetalization reaction):

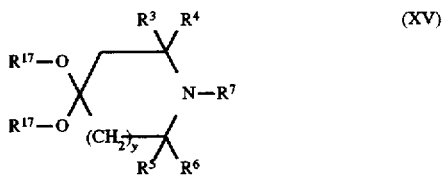

or a ketone of formula (XI) (acetalization reaction),
in which formulae the symbols $R^3$, $R^4$, $R^5$, $R^6$, $R^7$ and y have the general or preferential meanings given above with respect to the formula (II) and $R^{17}$ represents a linear or branched alkyl radical having from 1 to 3 carbon atoms.

As regards the way in which the abovementioned process is carried out in practice, reference should be made, for more details, to the contents of the following documents which describe, starting from other reactants, procedures applicable to carrying out the process under consideration: cf. transacetalization: Synthesis (February 1986), pages 122 to 125; acetalization: FR-A-2,168,848 (from Sankyo).

As regards the precursor ortho-diphenol of formula (XIV), it can be obtained by reacting:

a chlorinated compound of formula (XII)
with an ortho-diphenol or an acetal of formula:

As regards the way in which this synthesis of the precursor ortho-diphenol of formula (XIV) is carried out in practice, reference should be made, for more details, to the contents of the following document: cf. JP-A-53/135,943 (from Ube Industrie).

As regards the precursor acetal of formula (XV), it can be obtained by reacting, in a way known per se, an aliphatic alcohol of formula $R^{17}$—OH, in which $R^{17}$ has the meaning given above with respect to the formula (XV), with the ketone of formula (XI); cf. Synthesis (February 1986), pages 122 to 125.

The scheme, which has just been described, for the synthesis of the different unsaturated compounds (ψ) of formula (IX) where Z represents an aromatic residue applies particularly well when the symbol Z is the aromatic radical of formula (II-2) mentioned above and x is an integer equal to 1 or 2.

Whatever the definition of the aromatic symbol Z and the value of x, the crude product from the reaction of the reactant of formula (XVI) with the chlorinated compound of formula (XII) can contain small amounts of unreacted starting ortho-diphenol (XVI) and/or of diunsaturated compounds of formula:

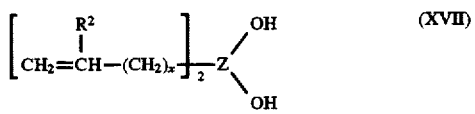

The crude product from the reaction under consideration will be purified, in the event of the presence of these impurities, in order to remove all or, failing that, most of these impurities. The crude product from the reaction can contain, without disadvantage, up to 2% by weight of these impurities.

The unsaturated compounds (ψ) of formula (IX) can also be formed by applying another synthetic scheme in which, in a first step, a cyclic acetal of formula:

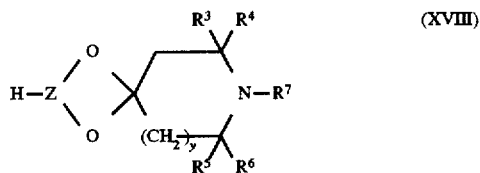

(XVIII)

is prepared and then, in a second step, the cyclic acetal of formula (XVIII) is reacted with a chlorinated compound of formula (XII). The cyclic acetal of formula (XVIII) can be prepared starting with a reactant of formula:

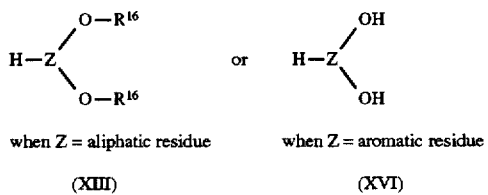

when Z = aliphatic residue        when Z = aromatic residue (XIII)                              (XVI)

by applying the various procedures described above with respect to the routes for the synthesis of the unsaturated compounds (ψ) of formula (IX), that is to say: reaction of the reactant (XIII) with the ketone (XI) or reaction of the reactant (XVI) with the acetal (XV) or the ketone (XI).

The unsaturated compounds (Ξ), from which the W functional groups derive, are compounds having an ethylenic unsaturation, situated at the chain end, capable of reacting in a hydrosilylation reaction in the presence of a catalyst based on a metal from the platinum group.

As compounds (Ξ), mention may be made, as examples, of 1-octene, 1-undecene, 1-dodecene, 1-tridecene, or methyl or ethyl undecenoate.

The optionally mixed polyorganosiloxanes according to the invention can be used as stabilizers in combating light, oxidative and thermal degradation of organic polymers, and this constitutes the third subject of the invention.

Mention may be made, as examples of such organic polymers, of polyolefins, polyurethanes, polyamides, polyesters, polycarbonates, polysulphones, polyethersulphones, polyetherketones, acrylic polymers, their copolymers and their mixtures.

Among these polymers, the compounds of the is invention have a more particularly effective action with polyolefins and polyalkadienes, such as polypropylene, high density polyethylene, linear low density polyethylene, low density polyethylene, polybutadiene, their copolymers and their mixtures.

Taking into account the wide possibilities of variations in the relative numbers of the various siloxy units present in the siloxane chain of the mixed compounds of the invention, these said compounds can be easily adaptable to the various problems to be solved.

Yet another subject of the present invention therefore consists in the compositions containing organic polymer stabilized against the harmful effects of heat and of UV by an effective amount of at least one optionally mixed polyorganosiloxane compound.

These compositions generally contain from 0.04 to 20 milliequivalents of sterically hindered cyclic amine functional group(s) per 100 g of polymer to be stabilized.

The polymeric compositions stabilized according to the invention preferably contain from 0.20 to 4 milliequivalents of sterically hindered cyclic amine functional group(s) per 100 g of polymer.

The addition of the optionally mixed polyorganosiloxane compounds can be carried out during or after the preparation of the polymers.

These compositions can additionally contain all the additives and stabilizers generally used with the polymers which they contain. Thus, it is possible to use the following stabilizers and additives: antioxidants, such as alkylated monophenols, alkylated hydroquinones, hydroxylated diphenyl sulphides, alkylidenebisphenols, benzyl compounds, acylaminophenols, esters or amides of 3-(3,5-di-tert-butyl-4-hydroxyphenyl)propionic acid or esters of 3-(3,5-dicyclohexyl-4-hydroxyphenyl)propionic acid; light stabilizers, such as optionally substituted benzoic acid esters, acrylic esters, nickel compounds or oxalamides; phosphites and phosphonites; metal deactivators; compounds which destroy peroxides; polyamide stabilizers; nucleation agents; fillers and reinforcing agents; or other additives, such as, for example, plasticizers, pigments, optical brighteners or flame retardants.

The polymer compositions thus stabilized can be applied in the most varied forms, for example in the form of moulded items, sheets, fibres, cellular materials (foam), sections or coating products, or as film-forming agents (binders) for paints, varnishes, adhesives or cements.

The following examples illustrate the present invention.

EXAMPLE 1

Preparation of the unsaturated compound (ψ) containing a cyclic amine functional group of formula (IX-2) in which $R^7$ is a hydrogen atom.

1) Preparation of the precursor of formula (XIV) consisting of 4-allyl-ortho-diphenol:

109.1 g (2.73 mol) of NaOH and 1522 g of water are charged to a round-bottomed glass flask equipped with a mechanical stirrer and a dropping funnel. After the NaOH has dissolved, 299.94 g (2.73 mol) of ortho-diphenol, 26.23 g (0.19 mol) of $CuCl_2$ and 33.93 g of an aqueous ammonia solution containing 28% by weight of $NH_4OH$ (i.e. 0.27 mol of ammonia base) are introduced.

A solution of 213 g (2.73 mol) of allyl chloride in isopropyl ether (270 g) is then run in over 1 h 15 minutes, at a temperature of between 36° C. and 56° C. On completion of the addition, the reaction is continued for 35 minutes at 50° C. At the end of this time, the reaction mixture is cooled to room temperature (23° C.) and then HCl (in the form of an aqueous solution containing 36% by weight of pure HCl) is run in until a pH equal to 3 is obtained.

The two phases which have formed are separated, the separation being carried out while warm (35° C.). The aqueous phase is then extracted 3 times with, each time, 200 cm³ of isopropyl ether. The organic phases are combined and the solution obtained is concentrated on a rotary evaporator, concentration being carried out between 25° C. and 40° C. under a reduced pressure of $3 \times 10^2$ Pa, and then it is neutralized with 4.3 g of sodium carbonate.

The crude product obtained is then purified by fractional distillation at 4 Pa; 244.8 g (yield of 60%) of 4-allyl-ortho-diphenol are obtained (boiling point under a pressure of 4 Pa: 146° C.; structure confirmed by proton nuclear magnetic resonance analysis).

2) Preparation of the precursor of formula (XV) consisting of the dimethyl acetal of 2,2,6,6-tetramethyl-4-piperidone (or triacetoneamine):

30 g (0.19 mol) of triacetoneamine and 51 g of methanol are charged to a round-bottomed glass flask which has been placed under a nitrogen atmosphere and which is equipped with a mechanical stirrer and a dropping funnel.

A solution of 31.97 g (0.192 mol) of sulphonic acid in 77 g of methanol is then run in slowly and then 40.6 g (0.38 mol) of methyl orthoformate are charged.

The reaction mixture is heated to reflux and the expected amount of methyl formate is distilled off. The methanol is then distilled off until precipitation takes place.

The crude product obtained is filtered off and then washed with two times 100 cm³ of toluene.

68 g (yield of 100%) of triacetoneamine dimethyl acetal are obtained. The structure of the product is confirmed by proton nuclear magnetic resonance.

3) Preparation of the unsaturated compound (ψ) of formula (IX-2) where $R^7$=H:

41.99 g (0.12 mol) of triacetoneamine dimethyl acetal, 18 g (0.12 mol) of 4-allyl-ortho-diphenol, 1.05 g (0.006 mol) of benzenesulphonic acid and 173 g of toluene are introduced into a round-bottomed glass flask equipped with a mechanical stirrer and a distillation column.

The reaction mixture is brought to 61° C., at which temperature boiling begins. The mixture is then distilled for 12 hours, a toluene-methanol azeotrope which distills between 60° and 70° C. at atmospheric pressure being continually removed.

The toluene is then removed and, after cooling to room temperature (23° C.), 200 cm³ of methylene chloride are added to the reaction mass.

The organic phase thus obtained is then washed with two times 150 cm³ of a 1N aqueous $NaHCO_3$ solution. The organic phase is dried over magnesium sulphate and the methylene chloride is then evaporated at room temperature (23° C.) under a pressure reduced to $1.33×10^2$ Pa.

26.7 g (yield of 50%) of the desired unsaturated product (ψ) of formula (IX-2) where $R^7$=H are thus obtained. Analysis by proton nuclear magnetic resonance is in agreement with the following structure, on which are shown the chemical shifts of the protons ($^1$H NMR; solvent: $CDCl_3$; 360 MHz):

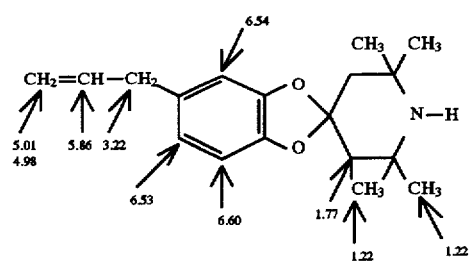

EXAMPLE 2

Preparation of a mixed organopolysiloxane 9.76 g (0.034 mol) of the unsaturated compound (ψ) prepared on conclusion of Example 1 and 10 cm³ of dry toluene are introduced into a 1 litre reactor equipped with a stirrer system and two dropping funnels and which is maintained internally under a dry nitrogen atmosphere. The reaction mixture is stirred and the temperature is brought to 90° C.

The following are then gradually run in simultaneously over a period of 5 hours:

4.12 g (i.e. 0.036 mol of Si—H functional groups) of a polymethylhydrosiloxane oil, the characteristics of which are as follows:

Mn=1630 g;
868 meq of SiH/100 g of oil;
average structure:

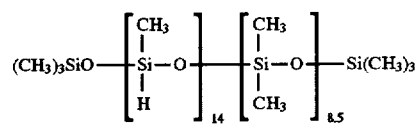

and 11 nm³ (or 11 μl) of a solution in toluene of a platinum catalyst (known as "Karstedt" catalyst) containing 11% by weight of Pt metal.

After having carried out the addition, the mixture is left to react for 36 hours at 90° C. At the end of this time, the degree of conversion of the Si—H functional groups is 92 mol %.

10 g (0.089 mol) of 1-octene are then added and the mixture is allowed to react for 16 hours at 90° C. The degree of conversion of the Si—H functional groups is 95 mol %.

The solvent is then removed by evaporation for 3 hours at 100° C. under a reduced pressure of $6.65×10^2$ Pa.

12 g of a clear oil are thus recovered, the characteristics of this oil being as follows:

Mn=5380 g;

235 meq of cyclic amine functional groups/100 g, for a theoretical value of 240 meq/100 g (this basicity value is measured by titrating the oil obtained using a 0.02N perchloric acid solution);

average structure of the oil:

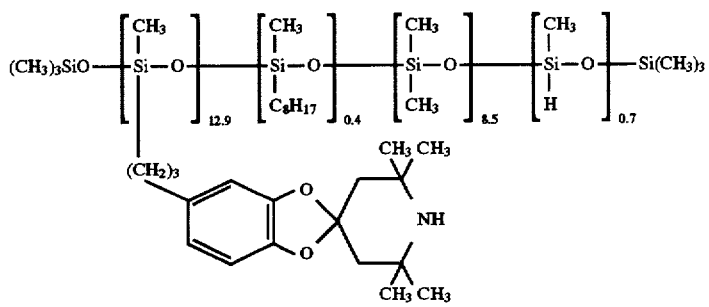

proportion of amine functional groups X: 52.6% (in moles of functional groups per 100 silicon atoms);
proportion of functional groups W: 1.6%.

EXAMPLE 3

Photostabilization of polypropylene

The following 2 compositions a and b are prepared in a slow mixer:

|  | a | b |
|---|---|---|
| Polypropylene, Eltex ® P HV001P (grade 10) | 100 g | 100 g |
| Stabilizer S1 according to Example 2, containing 235 meq of amine functional groups per 100 g of stabilizer | 0.2 g | — |
| Commercial stabilizer S2: Chimasorb 944 (cf. formula below), containing 341 meq of piperidyl functional groups per 100 g of stabilizer | — | 0.2 g |

Formula of Chimasorb 944:

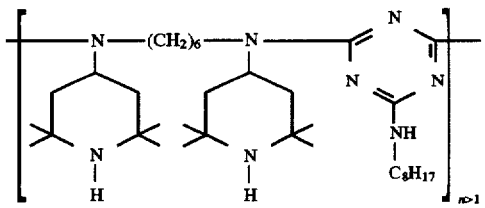

The abovementioned compositions are converted, under identical operating conditions, in order to result in films with a thickness of 200 μm.

The film based on polypropylene stabilized with S1 resulting from the composition a (Example 3) and the film based on polypropylene stabilized with S2 resulting from the composition b (Test b) are exposed to the same UV radiation. The aging of the films is monitored by infrared spectrometry. In each test, a measurement is made of the exposure time T to the UV rays necessary for the absorbence by infrared spectrometry of the carbonyl band (at 1720 cm$^{-1}$) resulting from oxidation to be equal to the absorbence 15 of a reference infrared band (CH$_2$ band at 2722 cm$^{-1}$); in other words, a measurement is made of the time T necessary in order to have, in each case, a degree of photo-oxidation such that:

$$\frac{\text{absorbence of the C=O band at 1720 cm}^{-1}}{\text{absorbence of the CH}_2 \text{ band at 2722 cm}^{-1}} = 1$$

It should be noted that the longer the time measured, the better is the protection conferred by the stabilizer (the C=O groups appear more slowly).

The results obtained are combined in the following table:

|  | Stabilized film | | Nonstabilized film |
|---|---|---|---|
|  | Example 3 | Test b | Control |
| Exposure time T to UV in hours | 80 | 70 | 20 |
| T/number of meq/100 g | 0.34 | 0.21 | |

What is claimed is:
1. A polyorganosiloxane comprising, per molecule, at least 3 siloxy units, including at least one siloxy functional unit of formula:

$$(R^1)_a X Si (O)_{\frac{3-a}{2}} \quad (I)$$

in which:
the symbols R$^1$ are identical or different and represent a monovalent hydrocarbon radical chosen from the linear or branched alkyl radicals having from 1 to 4 carbon atoms and the phenyl radical;
the symbol X represents a monovalent group of formula:

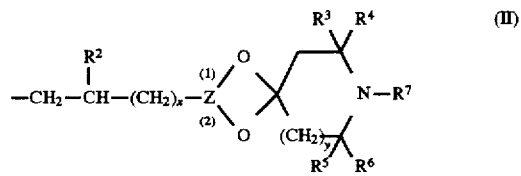

in which:
R$^2$ represents a hydrogen atom or a linear or branched alkyl radical having from 1 to 3 carbon atoms;
the symbol Z represents a trivalent group comprising at least 3 carbon atoms and selected from the group consisting of a substituted or unsubstituted, saturated or ethylenically unsaturated aliphatic radical which can contain at least one carbonyl group bonded via its free valencies to two atoms constituting the cyclic acetal group:

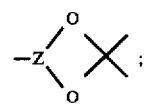

a substituted or unsubstituted monocyclic aromatic radical; a substituted or unsubstituted condensed polycyclic aromatic radical; and a polycyclic aromatic radical containing a number of substituted or unsubstituted, condensed or non-condensed cyclic systems which are bonded to one another via valency bonds or via atoms or groups;
the (1) and (2) bonds leaving from the symbol Z relate to adjacent carbon atoms when Z represents an aromatic radical and to adjacent carbon atoms or carbon atoms which are in the β position with respect to one another when Z represents an aliphatic radical;
the R$^3$, R$^4$, R$^5$ and R$^6$ radicals, which are identical or different, are selected from the group consisting of linear or branched alkyl radicals having from 1 to 3 carbon atoms, a phenyl radical and a benzyl radical;
R$^7$ is selected from the group consisting of a hydrogen atom, linear or branched alkyl radicals having from 1 to 12 carbon atoms, alkylcarbonyl radicals where the alkyl residue is a linear or branched residue having from 1 to 8 carbon atoms, phenyl and benzyl radicals and an O.radical;

x is an integer selected from the group consisting of 0, 1, 2 and 3;

y is 0 or 1;

a is a number selected from the group consisting of 0, 1 and 2.

2. The polyorganosiloxane according to claim 1 wherein the $R^1$ radicals are selected from the group consisting of methyl, ethyl, n-propyl, isopropyl and n-butyl.

3. The polyorganosiloxane according to claim 1 wherein the cyclic amine functional groups represented by the X groups are the radicals of formula (II) defined above in which the symbols $R^2$, $R^3$, $R^4$, $R^5$, $R^6$, $R^7$, x and y have the meanings given above with respect to the formula (II) and the symbol Z represents a trivalent radical selected from the group consisting of:

an aliphatic radical of formula:

$$-C R^{14} \begin{cases} CO- \\ CO- \end{cases} \quad (II-1)$$

where the thick right-hand free valencies are connected to the oxygen atoms of the cyclic acetal group and $R^{14}$ represents a hydrogen atom, a linear or branched alkyl radical having from 1 to 3 carbon atoms or a radical of formula $-COOR^{14a}$ or $-NHCOR^{14a}$ where $R^{14a}$ represents a linear or branched alkyl radical having from 1 to 3 carbon atoms; and an aromatic radical corresponding to the following formulae:

(II-2)   (II-3)

(II-4)

(II-5)

where the thick free valencies of each aromatic cyclic system are carried by two adjacent carbon atoms and $R^{15}$ represents —O—, —S—, a linear or branched alkylene group having from 1 to 3 carbon atoms, —CO—, —SO$_2$—, —CONH—, —NH— or —COO—.

4. The polyorganosiloxane according to claim 1 further comprising at least one other functional unit of formula:

$$(R^1)_b W Si(O)_{\frac{3-b}{2}} \quad (III)$$

in which:

the symbols $R^1$ have the same meanings as those given above with respect to the formula (I);

the symbol W represents a monovalent group containing a compatibilizing functional group selected from the group consisting of: a linear or branched alkyl radical having more than 4 carbon atoms; a radical of formula $-R^8-COO-R^9$ in which $R^8$ represents a linear or branched alkylene radical having from 5 to 20 carbon atoms and $R^9$ represents a linear or branched alkyl radical having from 1 to 12 carbon atoms; and a radical of formula $-R^{10}-O-(R^{11}-O)_c-R^{12}$ in which $R^{10}$ represents a linear or branched alkylene radical having from 3 to 15 carbon atoms, $R^{11}$ represents a linear or branched alkylene radical having from 1 to 3 carbon atoms, c is a number from 0 to 10 and $R^{12}$ represents a hydrogen atom, a linear or branched alkyl radical having from 1 to 12 carbon atoms or an acyl radical $-CO-R^{13}$ where $R^{13}$ represents a linear or branched alkyl radical having from 1 to 11 carbon atoms; b is a number chosen from 0, 1 and 2.

5. The polyorganosiloxane according to claim 4 wherein the compatibilizing functional groups W are selected from the group consisting of a linear or branched alkyl radical having from 5 to 18 carbon atoms; a radical of formula $-R^8-COO-R^9$ in which $R^8$ represents a linear or branched alkylene radical having from 8 to 12 carbon atoms and $R^9$ represents a linear or branched alkyl radical having from 1 to 6 carbon atoms; and a radical of formula $-R^{10}-O-(R^{11}-O)_c-R^{12}$ in which $R^{10}$ represents a linear or branched alkylene radical having from 3 to 6 carbon atoms, $R^{11}$ represents a linear or branched alkylene radical having from 2 to 3 carbon atoms, c is a number from 0 to 6 and $R^{12}$ represents a hydrogen atom, a linear or branched alkyl radical having from 1 to 6 carbon atoms or an acyl radical $-CO-R^{13}$ where $R^{13}$ represents a linear or branched alkyl radical having from 1 to 5 carbon atoms.

6. The polyorganosiloxane according to any one of claim 1 further comprising (an)other siloxy unit(s) of formula:

$$(R^1)_d(H)_e Si(O)_{\frac{4-(d+e)}{2}} \quad (IV)$$

in which:

the symbols $R^1$ have the same meanings as those given above with respect to the formula (I);

d is a number chosen from 0, 1, 2 and 3;

e is a number chosen from 0 and 1;

the sum d+e is not greater than 3.

7. The polyorganosiloxane according to claim 1 selected from the group consisting of:

statistical, sequenced or block, linear, optionally mixed polydiorganosiloxane copolymers of average formula:

$$Y-\underset{R^1}{\underset{|}{Si}}-O-\left[\underset{X}{\underset{|}{Si}}-O\right]_m\left[\underset{W}{\underset{|}{Si}}-O\right]_n\left[\underset{H}{\underset{|}{Si}}-O\right]_p\left[\underset{R^1}{\underset{|}{Si}}-O\right]_q\underset{R^1}{\underset{|}{Si}}-Y \quad (V)$$

in which:

the symbols $R^1$, X and W have the general meanings given above with respect to the formulae (I) and (III);

the symbols Y represent a monovalent radical chosen from $R^1$, X, W and a hydrogen atom;

m is a whole or fractional number ranging from 0 to 180;

n is a whole or fractional number ranging from 0 to 180;

p is a whole or fractional number ranging from 0 to 10;

q is a whole or fractional number ranging from 0 to 100; with the conditions according to which:

19 if m is other than 0 and, in the optional case of mixed polymers, if n is other than 0: the sum m+n+p+q lies in the range from 5 to 200; the ratio 100m/(m+n+p+q+2)≧0.5; and the ratio 100n/(m+n+p+q+2)≧0.5, this ratio being identical to or different from the preceding ratio;

if m=0 and, in the optional case of mixed polymers, if n is other than 0: at least one of the Y substituents represents the X radical; the sum m+n+p+q lies in the range from 5 to 100; and the ratio 100n/(m+n+p+q+2)≧0.5;

if m is other than 0 and n=0: the sum m+p+q lies in the range from 5 to 100; the ratio 100m/(m+p+q+2)≧0.5; and, in the case of mixed polymers, at least one of the Y substituents represents the W radical;

if m=0 and n=0: the sum p+q lies in the range from 5 to 100; one of the Y substituents being the X radical; and, in the case of mixed polymers, the other Y substituent being the W radical; and those of average formula:

$$\left[\begin{array}{c}R^1\\|\\Si-O\\|\\X\end{array}\right]_r\left[\begin{array}{c}R^1\\|\\Si-O\\|\\W\end{array}\right]_s\left[\begin{array}{c}R^1\\|\\Si-O\\|\\H\end{array}\right]_t\left[\begin{array}{c}R^1\\|\\Si-O\\|\\R^1\end{array}\right]_u \quad (VI)$$

in which:

the symbols $R^1$, X and W have the general meanings given above with respect to the formulae (I) and (III);

r is a whole or fractional number ranging from 1 to 9;

s is a whole or fractional number ranging from 0 to 9;

t is a whole or fractional number ranging from 0 to 0.5;

u is a whole or fractional number ranging from 0 to 5;

the sum r+s+t+u lies in the range from 3 to 10.

8. The mixed linear polyorganosiloxane according to claim 7 wherein:

the symbols Y represent $R^1$;

m is a whole or fractional number ranging from 1 to 90;

n is a whole or fractional number ranging from 1 to 90;

p is a whole or fractional number ranging from 0 to 5;

q is a whole or fractional number ranging from 0 to 50;

the sum m+n+p+q is a whole or fractional number ranging from 10 to 100;

the ratio 100m/(m+n+p+q+2) lies in the range from 8 to 90; with the condition according to which if n is other than 0, the ratio 100n/(m+n+p+q+2) lies in the range from 8 to 90, it being possible for this ratio to be identical to or different from the preceding ratio;

the $R^1$ radicals are selected from the group consisting of methyl, ethyl, n-propyl, isopropyl and n-butyl;

the X groups groups are the radicals of formula (II) defined above in which the symbols $R^2$, $R^3$, $R^4$, $R^5$, $R^6$, $R^7$, x and y have the meanings given above with respect

20 to the formula (II) and the symbol Z represents a trivalent radical selected from the group consisting of: an aliphatic radical of formula:

$$-C\underset{\diagdown CO-}{\overset{\diagup CO-}{R^{14}}} \quad (II\text{-}1)$$

where the thick right-hand free valencies are connected to the oxygen atoms of the cyclic acetal group and $R^{14}$ represents a hydrogen atom, a linear or branched alkyl radical having from 1 to 3 carbon atoms or a radical of formula —COOR$^{14a}$ or —NHCOR$^{14a}$ where $R^{14a}$ represents a linear or branched alkyl radical having from 1 to 3 carbon atoms; and an aromatic radical corresponding to the following formulae:

(II-2) ; (II-3) ;

(II-4) ;

(II-5)

where the thick free valencies of each aromatic cyclic system are carried by two adjacent carbon atoms and $R^{15}$ represents —O—, —S—, a linear or branched alkylene group having from 1 to 3 carbon atoms, —CO—, —SO$_2$—, —CONH—, —NH— or —COO—;

and the groups W are selected from the group consisting of a linear or branched alkyl radical having from 5 to 18 carbon atoms; a radical of formula —R$^8$—COO—R$^9$ in which R$^8$ represents a linear or branched alkylene radical having from 8 to 12 carbon atoms and R$^9$ represents a linear or branched alkyl radical having from 1 to 6 carbon atoms; and a radical of formula —R$^{10}$—O—(R$^{11}$—O)$_c$—R$^{12}$ in which R$^{10}$ represents a linear or branched alkylene radical having from 3 to 6 carbon atoms, R$^{11}$ represents a linear or branched alkylene radical having from 2 to 3 carbon atoms, c is a number from 0 to 6 and R$^{12}$ represents a hydrogen atom, a linear or branched alkyl radical having from 1 to 6 carbon atoms or an acyl radical —CO—R$^{13}$ where R$^{13}$ represents a linear or branched alkyl radical having from 1 to 5 carbon atoms.

9. The mixed cyclic polyorganosiloxane according to claim 7 wherein:

r is a whole or fractional number ranging from 1 to 4.5;

s is a whole or fractional number ranging from 1 to 4.5;

t is a whole or fractional number ranging from 0 to 0.25;

u is a whole or fractional number ranging from 0 to 2.5;

the sum r+s+t+u is a whole or fractional number ranging from 3 to 5;

the $R^1$ radicals are selected from the group consisting of methyl, ethyl, n-propyl, isopropyl and n-butyl;

the X groups groups are the radicals of formula (II) defined above in which the symbols $R^2$, $R^3$, $R^4$, $R^5$, $R^6$, $R^7$, x and y have the meanings given above with respect to the formula (II) and the symbol Z represents a trivalent radical selected from the group consisting of: an aliphatic radical of formula:

where the thick right-hand free valencies are connected to the oxygen atoms of the cyclic acetal group and $R^{14}$ represents a hydrogen atom, a linear or branched alkyl radical having from 1 to 3 carbon atoms or a radical of formula —COOR$^{14a}$ or —NHCOR$^{14a}$ where $R^{14a}$ represents a linear or branched alkyl radical having from 1 to 3 carbon atoms; and an aromatic radical corresponding to the following formulae:

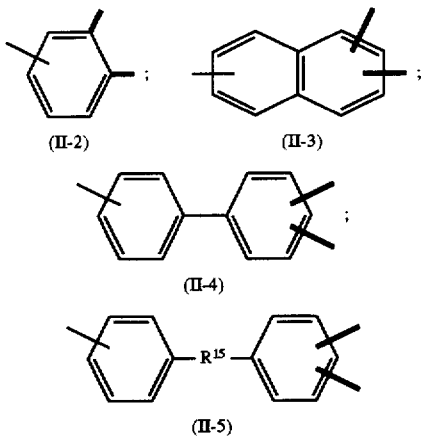

where the thick free valencies of each aromatic cyclic system are carried by two adjacent carbon atoms and $R^{15}$ represents —O—, —S—, a linear or branched allylene group having from 1 to 3 carbon atoms, —CO—, —SO$_2$—, —CONH—, —NH— or —COO—;

and the groups W are selected from the group consisting of a linear or branched alkyl radical having from 5 to 18 carbon atoms; a radical of formula —R$^8$—COO—R$^9$ in which R$^8$ represents a linear or branched alkylene radical having from 8 to 12 carbon atoms and R$^9$ represents a linear or branched alkyl radical having from 1 to 6 carbon atoms; and a radical of formula —R$^{10}$—O—(R$^{11}$—O)$_c$—R$^{12}$ in which R$^{10}$ represents a linear or branched alkylene radical having from 3 to 6 carbon atoms, R$^{11}$ represents a linear or branched alkylene radical having from 2 to 3 carbon atoms, c is a number from 0 to 6 and R$^{12}$ represents a hydrogen atom, a linear or branched alkyl radical having from 1 to 6 carbon atoms or an acyl radical —CO—R$^{13}$ where R$^{13}$ represents a linear or branched alkyl radical having from 1 to 5 carbon atoms.

10. A process for the preparation of an optionally mixed polyorganosiloxane according to claim 1 comprising the steps of:

in the case of polymers containing solely cyclic amine functional group(s): an addition (hydrosilylation) reaction, or in the case of mixed polymers containing cyclic amine functional group(s) and containing compatibilizing functional group(s): two simultaneous or successive addition (hydrosilylation) reactions, starting with: the corresponding organohydropolysiloxanes (H) free of the X and W functional groups, the organic compound(s) which is(are) ethylenically unsaturated at the chain end (ψ), from which the X functional group(s) derive (s), and optionally the compound(s) which is(are) ethylenically unsaturated at the chain end (Ξ), from which the W functional group(s) derive(s), and in that the amounts of the reactants involved correspond to a [(ψ)+optionally (Ξ)]/SiH molar ratio which varies from 1 to 5.

11. The process according to claim 10 wherein the unsaturated organic compounds (ψ), from which the X groups containing a cyclic amine functional group derive, are the compounds of formula:

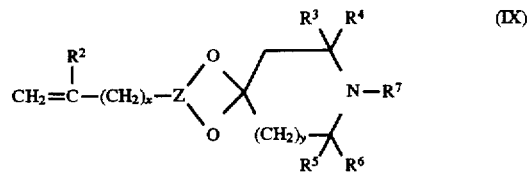

in which the symbols $R^2$, Z, $R^3$, $R^4$, $R^5$, $R^6$, $R^7$, x and y have the meanings given above with respect to the formula (II).

12. The process according to claim 11 wherein the unsaturated organic compounds (ψ) of formula (IX) in which the symbol Z represents an aliphatic residue are prepared by reacting, in the presence of an acid catalyst:

an ortho-diphenol or an acetal of formula:

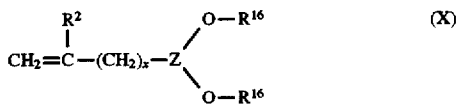

in which the symbols $R^2$, Z (aliphatic residue) and x have the meanings given above with respect to the formula (II) and $R^{16}$ represents a hydrogen atom or a linear or branched alkyl radical having from 1 to 3 carbon atoms, with a ketone of formula:

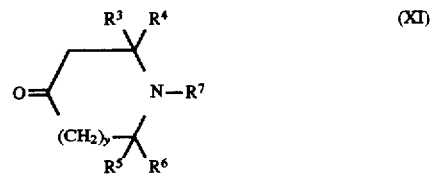

in which the symbols $R^3$, $R^4$, $R^5$, $R^6$, $R^7$ and y have the meanings given above with respect to the formula (II).

13. The process according to claim 11, wherein the unsaturated organic compounds (ψ) of formula (IX) in which the symbol Z represents an aromatic residue are prepared by reacting, in the presence of an acid catalyst:

23 an ortho-diphenol of formula:

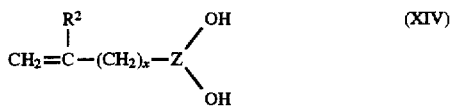

(XIV)

in which the symbols $R^2$, Z (aromatic residue) and x have the meanings given above with respect to the formula (II), with:

either an acetal of formula (transacetalization reaction):

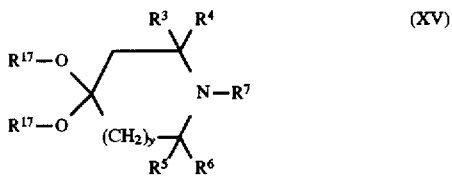

(XV)

or a ketone of formula (XI) (acetalization reaction), in which formulae the symbols $R^3$, $R^4$, $R^5$, $R^6$, $R^7$ and y have the meanings given above with respect to the formula (II) and $R^{17}$ represents a linear or branched alkyl radical having from 1 to 3 carbon atoms.

14. The process according to claim 11 wherein the unsaturated organic compounds (ψ) of formula (IX) are prepared by reacting a cyclic acetal of formula:

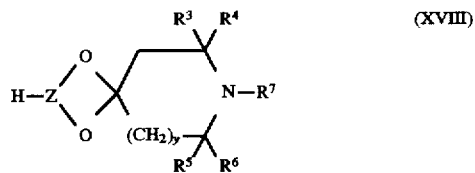

(XVIII)

24 with a chlorinated compound of formula:

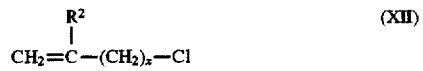

(XII)

in which formulae the symbols Z, $R^3$, $R^4$, $R^5$, $R^6$, $R^7$, y, $R^2$ and x have the meanings given above with respect to the formula (II).

15. The process of stabilizing organic polymers against light and oxidative and thermal degradation comprising the step of adding a stabilizing effective amount of a polyorganosiloxane according to claim 1.

16. The process of stabilizing organic polymers according to claim 15 wherein the organic polymers to be stabilized are selected from the group consisting of polyolefins, polyurethanes, polyamides, polyesters, polycarbonates, polysulphones, polyethersulphones, polyetherketones, acrylic polymers, their copolymers and their mixtures.

17. An organic polymer composition stabilized against light, oxidative and thermal degradation comprising:

per 100 g of organic polymer to be stabilized, an amount of polyorganosiloxane according to claim 1 introducing from 0.04 to 20 milliequivalents of sterically hindered cyclic amine functional group(s).

18. The composition according to claim 17 wherein the organic polymers to be stabilized are selected from the group consisting of polyolefins, polyurethanes, polyamides, polyesters, polycarbonates, polysulphones, polyethersulphones, polyetherketones, acrylic polymers, their copolymers and their mixtures.

* * * * *